United States Patent [19]

Lane et al.

[11] Patent Number: 4,976,682
[45] Date of Patent: Dec. 11, 1990

[54] METHODS AND APPARATUS FOR AUTOLOGOUS BLOOD RECOVERY

[76] Inventors: Perry L. Lane, 2798 Arcadia Heights Cir., Salt Lake City, Utah 84109; Udipi R. Shettigar, 1021 Medical Plz., Salt Lake City, Utah 84112

[21] Appl. No.: 272,241

[22] Filed: Nov. 16, 1988

Related U.S. Application Data

[63] Continuation-in-part of Ser. No. 123,809, Nov. 23, 1987, abandoned.

[51] Int. Cl.$^5$ .............................................. A61M 1/03
[52] U.S. Cl. .......................................................... 604/4
[58] Field of Search .......................................... 604/4-6, 604/27-28, 266, 269

[56] References Cited

U.S. PATENT DOCUMENTS

| | | |
|---|---|---|
| 478,872 | 7/1982 | Kirkwood . |
| 1,114,268 | 10/1914 | Kells . |
| 2,804,075 | 8/1957 | Borden . |
| 3,191,600 | 6/1965 | Everett . |
| 3,412,510 | 1/1969 | Kettenbach . |
| 3,542,031 | 11/1970 | Taylor ............................. 128/304 |
| 3,623,483 | 11/1971 | Hyer, Jr. ............................ 128/276 |
| 3,680,560 | 8/1972 | Pannier, Jr. et al. ............... 128/276 |
| 3,685,517 | 8/1972 | Reynolds et al. ................... 128/277 |
| 3,704,709 | 12/1972 | Sorenson et al. ................... 128/277 |

(List continued on next page.)

FOREIGN PATENT DOCUMENTS 3321466.2  6/1983  Fed. Rep. of Germany .

OTHER PUBLICATIONS

Autotransfusion Reference Materials, Electromedics, Inc.
"The Hematology of Autotransfusion", William Bell, M.D. 84 Surgery, 695 (Nov. 1978).
"An Appraisal of Blood Salvage Techniques in Vascular and Cardiac Operations", A. Robert Cordell, M.D., and Sidney W. Lavender, M.M.Sc., 31 Annals of Thoractic Surgery, 421 (May 1981).
"Autotransfusions", Hauer, 300 New England Journal of Medicine at 1276 (May 1979).
"The Efficacy of Postoperative Autotransfusion in Patients Undergoing Cardiac Operations", Robert G. Johnson, M.D. et al., 36 Annal of Thoractic Surgery, 183 (Aug. 1983).
"Pleur-Evac Autotransfusion System", Deknatel, Product Brochure.
"Routine Use of Autotransfusion Following Cardiac Surgery: Experience in 700 Patients", Hartzell V. Schaff, M.D., et al., 27 Annals of Thoractic Surgery, 493 (Jun. 1979).
"Autotransfusion Following Cardiac Operations: A Randomized, Prospective Study", Robert L. Thurer, M.D., et al., 27 Annals of Thoractic Surgery, 500 (Jun. 1979).
"An Improved Method for Collection of Shed Mediastinal Blood for Autotransfusion", L. Dieter Voegele, M.D., et al., 32 Annals of Thoractic Surgery, 471.

Primary Examiner—C. Fred Rosenbaum
Assistant Examiner—K. Daley

[57] ABSTRACT

Improved methods and apparatus for the collection, purification and reinfusion of blood from a wound site. The present invention provides a source of anticoagulated washing fluid in proportion to the bleeding rate which can be directed to the suction tip in such a way that the wound or surgical site is washed.

The present invention minimizes blood damage and maximizes blood recovery by (i) automatically regulating the suction in proportion to the bleeding rate, (ii) minimizing the air suction or blood frothing, (iii) washing the wound site with the anticoagulated washing fluid, and (iv) reducing the number of blood pumps, preferably to one.

The present invention also provides a system to operate automatically by including automatic venting of entrapped air, continuous determination of irrigation fluid added into the wound site and its removal, continuous monitoring of hematocrit, continuous neutralization of anticoagulant, and reinfusion of purified blood to patient on realtime basis irrespective of bleeding rate.

59 Claims, 4 Drawing Sheets

U.S. PATENT DOCUMENTS

| | | | |
|---|---|---|---|
| 3,849,071 | 11/1974 | Kayser | 23/258.5 |
| 3,863,634 | 2/1975 | Reynolds et al. | 128/276 |
| 3,866,608 | 2/1975 | Reynolds et al. | 128/276 |
| 3,929,126 | 12/1975 | Corsault | 128/240 |
| 3,955,573 | 5/1976 | Hansen et al. | 128/276 |
| 3,958,573 | 5/1976 | Wiley | 128/276 |
| 3,964,484 | 6/1976 | Reynolds et al. | 128/276 |
| 3,965,896 | 6/1976 | Seank | 128/214 R |
| 3,993,067 | 11/1976 | Schachet et al. | 128/214 C |
| 4,002,170 | 1/1977 | Hansen et al. | 128/276 |
| 4,004,590 | 1/1977 | Muriot | 128/276 |
| 4,006,745 | 2/1977 | Sorenson et al. | 128/214 R |
| 4,014,329 | 3/1977 | Welch et al. | 128/214 R |
| 4,047,526 | 9/1977 | Reynolds et al. | 128/214 R |
| 4,068,664 | 1/1978 | Sharp et al. | 128/276 |
| 4,191,182 | 3/1980 | Popvich et al. | 128/214 R |
| 4,205,677 | 6/1980 | Engstrom | 128/276 |
| 4,299,705 | 11/1981 | Russell | 210/647 |
| 4,321,921 | 3/1982 | Laszczower | 128/276 |
| 4,368,118 | 1/1983 | Siposs | 210/136 |
| 4,411,786 | 10/1983 | Russell | 210/321.3 |
| 4,424,053 | 1/1984 | Kurtz et al. | 604/4 |
| 4,430,084 | 2/1984 | Deaton | 604/317 |
| 4,435,170 | 3/1984 | Laszczower | 604/4 |
| 4,443,220 | 4/1984 | Hauer et al. | 604/408 |
| 4,466,888 | 8/1984 | Verkaart | 210/232 |
| 4,487,600 | 12/1984 | Brownlie et al. | 604/35 |
| 4,493,705 | 1/1985 | Gordon et al. | 604/122 |
| 4,500,308 | 2/1985 | Kurtz et al. | 604/4 |
| 4,540,406 | 9/1985 | Miles | 604/269 |
| 4,547,186 | 10/1985 | Bartlett | 604/4 |
| 4,631,050 | 12/1986 | Reed et al. | 604/4 |
| 4,643,713 | 2/1987 | Viitala | 604/4 |
| 4,692,140 | 9/1987 | Olson | 604/40 |
| 4,708,714 | 11/1987 | Larsson et al. | 604/6 |
| 4,715,848 | 12/1987 | Beroza | 604/35 |
| 4,736,748 | 4/1988 | Nakamura et al. | 604/5 |
| 4,796,644 | 1/1989 | Polaschegg | |
| 4,828,543 | 5/1989 | Wiess et al. | 604/6 |
| 4,838,865 | 6/1989 | Plank et al. | 604/4 |
| 4,850,995 | 7/1989 | Tie et al. | 604/6 |
| 4,850,998 | 7/1989 | Schoendorfer | 604/6 |
| 4,886,487 | 12/1989 | Solem et al. | 604/5 |

METHODS AND APPARATUS FOR AUTOLOGOUS BLOOD RECOVERY

BACKGROUND

1. Field of the Invention

The present invention relates to methods and apparatus for recovery and reinfusion of blood lost at a wound site, such as during an operation. In particular, the present invention is related to recovering and reinfusing blood without significant damage to the blood cells, denaturation of proteins, or other damage to the reinfused blood supply.

2. Related Application

This application is a continuation-in-part application of the inventors copending application Ser. No. 07/123,809, filed Nov. 23, 1987 entitled "Autologous Blood Recovery System and Method," and now abandoned.

THE BACKGROUND OF THE INVENTION

It is well accepted in the art that when a person loses a significant quantity of blood, it may be necessary to transfuse to that person homologous (donor) blood as part of the individual's treatment. In these situations, blood from a donor is generally injected into the patient's system in order to compensate for blood loss.

Blood transfusions are required in several different and definable contexts. When a serious trauma occurs with significant resulting loss of blood, the situation may well dictate that additional blood be transfused to the patient as part of the patient's treatment. Similarly, in the context of serious and traumatic surgery, such as heart surgery, it is generally necessary to add blood to the patient's system to make up for blood lost during the surgical procedure.

At the same time, medical personnel find that during surgery it is highly desirable that any blood and fluid which accumulates in the surgical site be transported away from the operative field. This provides the surgeon with a clear view of the surgical area. Generally, suction is provided in order to remove blood, accumulated fluid, and other small particulate debris from the surgical site.

Thus, in the situations mentioned above, significant amounts of blood may be lost due simply to the extent of the injury or the extent of the surgery. At the same time, in order to clear the relevant area such that repair can be undertaken by the medical team, blood and other fluids are generally intentionally removed by suction. Thus, unless the blood lost or removed can be salvaged in some manner, it is necessary to give the patient homologous blood to compensate for blood lost.

One of the problems encountered in recovering blood from the surgical or wound site is that undesirable substances are often mixed with the blood. Some of the undesirable substances often recovered in such blood include solid particulate debris, including cell fragments, small platelet clots, damaged lucocytes, or other clotted cells or fibrin. In addition, tissue fragments and other foreign material are frequently found in the wound, depending on the cause of the wound. When salvaging blood from an operative field, it is, of course, the goal to recover healthy blood cells together with associated plasma. However, these undesirable substances often render the blood unsuitable for reinfusion unless extensive purification can take place.

Because of these foreign substances which may be contained within the blood, it is conventionally the practice that if the blood is to be salvaged it is necessary to "wash" the blood using any one of a number of known $ washing techniques. These techniques may include adding fluid to the blood and then centrifuging the blood in order to recover the heavier intact blood cells. The blood cells, along with autologous plasma, are then suitable for reinfusion. Alternatively, it may be possible to recover sufficient plasma to allow the blood cells to be resuspended and reinfused. In any event standard blood washing techniques are slow and can only produce cells and plasma for reinfusion at a later time.

Thus, it will be appreciated that existing washing techniques are not adaptable to continuous blood processing. Such techniques are usually limited to batch processing of blood collected, and use of that blood at a later time once the processing has been completed. Further, blood washing devices generally cannot be interrupted to produce usable blood products once the process has begun. This is primarily due to the fact that blood is not ready to be returned to the patient until it has been completely processed. Thus, when the need arises, a patient must often receive a homologous blood transfusion rather than his own blood which is still being processed.

Problems with the use of these techniques have been compounded due to several situations which have recently developed in transfusing homologous blood. One such problem is that donor blood is becoming more and more scarce. With the increasing demand for homologous blood, there has been a corresponding decrease in the amount of donor blood available. As a result, it is at times difficult to obtain the blood necessary to complete needed transfusions. In the event blood is found available, the cost of that blood is generally quite great. A donor blood transfusion can add significantly to the cost of treatment.

In addition, certain adverse reactions have been experienced when using homologous blood. Immune and allergic reactions are possible and have been encountered. Such on a patient. Likewise, homologous blood can at effects on a patient. Likewise, homologous blood can at times carry diseases. Hepatitis is commonly transmitted through homologous blood. There is also considerable concern about the transfusion of other serious diseases such as acquired immune deficiency syndrome (AIDS) and malaria.

As a result of the problems discussed above, the possibility of providing "autotransfusion" (reuse of a patient's own blood) of autologous blood has received increasing attention. This is true, even though the existing methods have been found to be quite inadequate.

Many of the known devices for use in autotransfusion simply comprise containers capable of receiving blood lost by a patient. In addition, it has been quite popular in the past to provide a container which is placed in communication with a source of vacuum. As a result, the blood is drawn into the container from the surgical or trauma area by a strong vacuum force. The vacuum source may be the operating room vacuum or it may be an independent source of suction.

Some containers of this general sort have been modified by placing disposable liners within the interior of the container and then providing a vacuum to drive the blood into the disposable liner. This type of container is conventionally used to collect blood and other fluids for disposal rather than reinfusion. The container is not modified in order to remove the impurities which may have accumulated within the collected blood.

While various configurations of autologous transfusion devices have been developed, the basic principles of operation have essentially remained the same. Blood is forced into a device under a high vacuum with a large airflow across the blood air interface. A large amount of air is necessarily mixed with the blood collected, resulting in foaming of the blood and production of air emboli. Once the blood is collected within the collection container, it is then either immediately reinfused, transferred to a separate container, or discarded.

One of the severe problems with the existing devices is damage to the blood collected. This damage may take the form of hemolysis, clot formation, or "drying" of the blood as it is collected. In addition, the mixture of air within the plasma can cause significant protein denaturation. Some of the primary factors causing damage to the blood include the high vacuum under which many devices operate, coupled with extensive mixing between air and blood within the system. This mixing and vacuum results in damage to the blood, rupture of blood cells, protein denaturation, foaming, and the formation of clots and emboli.

Another problem in existing autotransfusion systems is in providing adequate filtration of the blood once it is collected. It is not unusual for impurities, tissue fragments emboli or other particulate matter to be collected within the blood. As a result, it is critical that adequate filtering be provided. Existing devices, however, have found it difficult to provide necessary blood filtering during the process.

It is apparent that what is needed in the art are methods and apparatus for easily and effectively collecting and transfusing blood. It would be an advancement in the art to provide such methods and apparatus which were capable of providing reinfusion of blood on a real time basis. That is, reinfusion such that the delays encountered in batch washing processes are eliminated and that blood removed during an operation could be returned to the patient during the same operation (or shortly thereafter).

It would also be an advancement in the art to provide such methods and apparatus which would minimize the air blood interaction during blood collection. Similarly, it would be a significant advancement in the art to provide such methods and apparatus which operated at relatively low vacuum in order to prevent blood and protein damage. It would be a further advancement to provide such methods and apparatus which include adequate blood filtering and air removal such that reinfused blood is of high quality.

It would be a further advantage to provide an autotransfusion apparatus which incorporated automatic controls. It would be a related advantage to have the ability to automatically regulate suction in proportion to the bleeding rate. It would be an advantage to provide a system for determining bleeding rate automatically. It would also be an advantage to minimize the number of blood pumps employed in order to minimize blood damage.

Such methods and apparatus are disclosed and claimed herein.

BRIEF SUMMARY AND OBJECTS OF THE INVENTION

The present invention is directed to improved methods and apparatus for the collection and reinfusion of blood from a wound site. The present invention overcomes the limitations and problems in the prior art which have been discussed above. The present invention provides a system which operates with low vacuum and which minimizes or eliminates air blood interfaces during collection and within the interior of the system. The present invention also provides the capability of immediately reinfusing blood collected from a patient.

The present invention provides a source of fluid which can be directed into the wound or surgical site. This fluid may be any type of conventional fluid used in surgery, such as heparinized normal saline or Ringer's solution. The stream of fluid can be directed onto the area which is producing the blood so that the surgeon can readily detect the exact location of the bleeding. The fluid will, therefore, remove accumulated blood and the source of new blood can be readily detected as it enters the clear fluid stream.

The fluid also serves as a cell washing fluid. For this reason the flow rate of the fluid is kept at least equal to the bleeding flow rate and as the bleeding rate increases, the fluid flow rate increases correspondingly. When there is little or no bleeding, the fluid flow rate is maintained at a low minimum level, such as approximately 15 milliliters per minute. Through the use of a microprocessor which obtains information from bubble detectors placed in strategic locations in the system, it is possible to automatically increase or decrease the amount of fluid in response to changes in the rate of bleeding. When bubbles are detected in the system, the fluid flow rate increases. When no bubbles are detected the flow rate decreases.

The present invention also provides a submersible suction tip for gathering blood and other fluids. The submersible suction tip is placed in the accumulated mixture of blood and fluid at the wound or surgical site. The open portion of the suction tip is entirely submersed in the mixture such that no air is drawn into the tip. Vacuum is provided to the submersible suction tip by means of a roller pump or the like which is located downstream from the submersible tip. The submersible suction tip coupled with the flow of fluid to the wound site decreases dwell time for the blood at the wound site and, therefore, minimizes clotting and coagulation reactions.

In one embodiment of the present invention the suction tip and the terminal end of the washing fluid line are integral, and may be encircled by a shroud. As a result, the washing fluid is provided to the end of the suction tip such that blood entering the suction tip mixing immediately with the fluid and need not contact and mix with air. This eliminates one major source of blood damage encountered in conventional devices.

The submersible suction tip is attached to a suction or collection tube, which in turn conveys the blood-fluid mixture collected into a collection vessel. Because of the method of collecting blood, conventional defoaming units are not required. However, within the collection vessel any air bubbles which may have accumulated will rise to the top. The collection vessel, therefore, is provided with a blood level detector and vent.

When the fluid level within the collection vessel drops below a predetermined level, the fluid level detector is actuated to open the vent such that the accumulated air may be removed. At the same time fluid may be added to the collection vessel until the fluid level rises to the desired acceptable level. Venting can also be controlled automatically in response to a blood level detector. This method provides effective removal of air which has accumulated in the blood-fluid mixture even though significant air accumulations will not be expected because of the combination of the submersible suction tip and the low level suction employed.

Also preferably included within the collection vessel is a macrofilter assembly. The macrofilter assembly is provided in order to remove from the blood flow any relatively large particulate debris, such as emboli, accumulations of cell walls, and other debris collected at the surgical or wound site.

Once the blood is collected and filtered within the collection vessel, the blood may flow out through a blood collection vessel outlet line through the blood roller pump described above and into a filter vessel.

The filter vessel may contain a plasma membrane separator. The plasma membrane separator is a filter of the type conventionally used in the art. It is presently preferred that the plasma membrane separator have a pore size in the range of approximately 0.2 to approximately 0.5. A filter with a minimum surface area of $0.3m^2$ is presently preferred. Such filters can be obtained from several manufacturers including: Cobe Laboratories, Inc.; Fresenius A. G., West Germany; Asahi, Japan; and Travenol Labs. It is also presently preferred that plasma separation take place at a transmembrane pressure (TMP) of less than approximately 100 mm Hg in order to minimize hemolysis.

In some embodiments of the present invention the plasma membrane separator separates the blood cells from the plasma. It will be appreciated that the blood cells, as that term is used herein, includes a suspension of blood cells in a relatively small amount of plasma. Essentially all of the plasma, except for that amount necessary to suspend the blood cells, can be removed as it flows through the filter vessel.

In one embodiment of the invention, blood cells leave the filter vessel through a blood cell outlet line, while plasma leaves the filter vessel through a plasma outlet line. The plasma outlet line then passes through an additional roller pump, generally referred to as a plasma pump, and finally flows into an ultrafilter vessel. The ultrafilter vessel removes excess fluid and activated coagulation factors from the plasma. The ultrafilter preferably has a pore size cut off of approximately 60,000 daltons such that fluid and activated coagulation factors are removed from the plasma at this point. The ultrafilter may be any one of a number of commercially available ultrafilters available from manufacturers such as Amicron Corporation, Asahi, Fresenius A. G., Travenol Labs and others. An ultrafilter with a minimum surface area of $0.3m^2$ is presently preferred.

The plasma may then be directed through a multiadsorbent bed whereby accumulated toxins are removed from the plasma. The plasma is then preferably recombined with the washed blood cells in order to form reconstituted blood. This reconstituted blood is then directly reintroduced to the patient.

It will be appreciated that either the plasma or the blood cells may be discarded at any point in the process, depending on the quality of the specific blood component. For example, a hemoglobin detector may be placed on the plasma outlet line, or at any other point along the flow path of the plasma. The hemoglobin detector allows the physician or technician to determine whether or not unacceptably high levels of hemoglobin are contained within the plasma. If high hemoglobin levels are detected, the plasma may simply be discarded.

Likewise, if the blood cells separated were for some reason undesirable or unneeded, they can be discarded prior to reinfusion.

Alternatively, filtered whole blood may be passed through an ultrafilter or plasma filter which removes excess liquids. Such liquids will comprise the washing fluid and any fluids added at the wound site.

It will be appreciated that the systems of the present invention preferably also include one or more bubble detectors. It is presently preferred that commercially available ultrasonic bubble detectors be employed. The bubble detectors allow the physician or technician to avoid infusing air along with the plasma and blood cells. In addition, bubble detectors may be employed to automatically control the volume of liquids flowing at various locations in the circuit, and other similar functions.

It may be desirable, for example, to have a bubble detector on the suction tube such that bubbles collected will be immediately detected. Likewise, it may be desirable to have a bubble detector in conjunction with the collection vessel so that excess air content may be detected at that point. It may also be desirable to have a bubble detector in connection with blood line prior to reinfusion to patient so that bubbles can be immediately detected prior to infusion.

It will be appreciated that the present invention, when compared with conventional existing devices, reduces hemolysis and other types of cell damage, as well as foaming and protein denaturation. The present invention minimizes any blood air contact, eliminates the need for defoaming units, and also eliminates the need for a high vacuum. Thus, the major causes of blood damage encountered in existing autotransfusion devices are eliminated.

It is, therefore, an object of the present invention to provide an effective collection and autotransfusion system for collecting blood from a wound or surgical site and reinfusing that blood to a patient.

It is a further object of the present invention to provide such an autotransfusion system which is able to reinfuse blood on a "real time" basis.

It is another object of the present invention to provide an autotransfusion system which essentially eliminates blood-air interfaces and blood-air mixing.

It is still another object of the present invention to provide an autotransfusion system that is able to operate at low suction.

It is a further object to minimize blood damage by minimizing the number of blood pumps used and by minimizing air intake and frothing.

It is another object of the present invention to make necessary adjustments automatically.

Finally, it is an object of the present invention to automatically determine the volume of irrigation fluid added and to subsequently remove the fluid from the blood prior to reinfusion.

These and other objects of the invention will become apparent upon reading the following detailed description and appended claims and upon reference to the accompanying drawings.

DETAILED DESCRIPTION OF THE PREFERRED EMBODIMENTS

It will be appreciated that the components of the present invention, as generally described and illustrated in the figures below, could be arranged and designed in a wide variety of configurations. Thus, the following detailed description of representative embodiments of the systems and methods of the present invention are not intended to limit the scope of the invention as claimed, but are representative of possible embodiments of the present invention.

The present invention can be better understood by reference to the drawings, wherein like parts are designated by like numerals throughout. One embodiment of the present invention can be better understood by reference to FIG. 1 which comprises a flow diagram or schematic which illustrates a first embodiment of the present invention.

Figure 1:
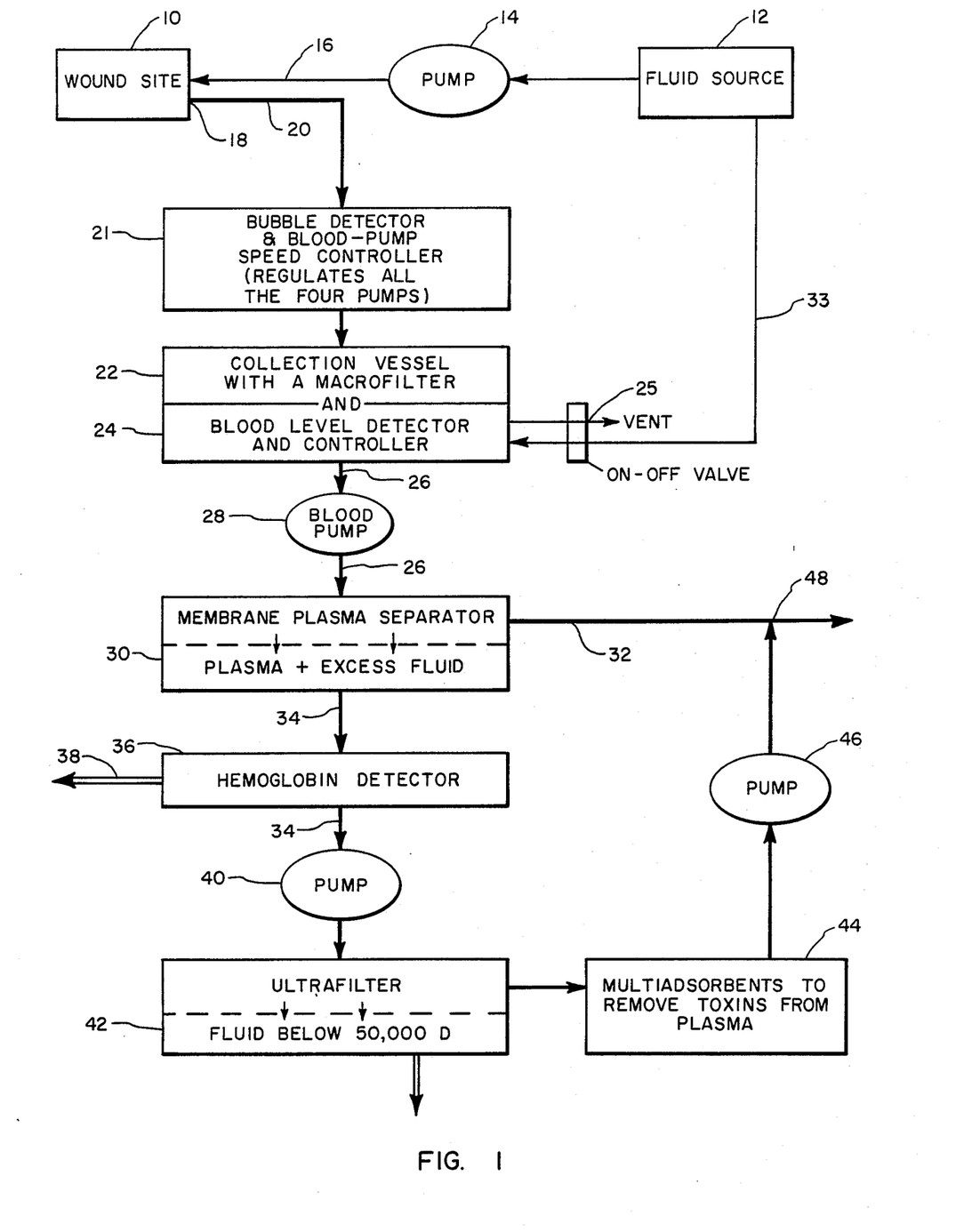
FIG. 1 is a schematic diagram illustrating the steps and features of one embodiment the apparatus and methods of the present invention.

As can be seen in FIG. 1, the location of a wound site is shown generally and is designated 10. The wound site 10 could be any location at which a patient is losing blood. The most common wound sites are likely to be surgical sites or the location of a serious trauma.

The present invention provides a source of fluid which will be introduced, in the form of a controlled stream, to the wound site. This source of fluid 12 is generally illustrated in FIG. 1. The fluid may be pumped from the source of fluid 12 to the wound site 10 using pump 14. Pump 14 may be any type of fluid pump such as a conventional roller pump for forcing fluid through a tube. Pump 14 drives the fluid along fluid supply line 15. The fluid supply line 16 terminates at the wound site. It will be appreciated that any type of conventional controlled nozzle may also be used at the end of fluid supply line 16 such that a controlled flow of fluid will be provided to the wound site. Specific embodiments of this portion of the device will be described in further detail below.

The fluid pumped by pump 14 through fluid supply line 16 is used to wash the wound or surgical area. In addition, the fluid is used as a cell washing fluid in order to wash cells as they enter the filter vessel described below. This washing removes blood from the surgical site and also allows the surgeon to determine the source of bleeding, in that the blood entering the clear fluid will be readily detectable. The fluid also results in a reduction of dwell time of the blood in the wound site such that clotting and coagulation reactions are minimized. The fluid used will likely be conventional heparinized saline or Ringer's solution. Other solutions may also be acceptable in specific circumstances. As will be discussed below, the flow rate of the washing fluid can be regulated automatically to be proportional to the bleeding rate.

The accumulated fluid and blood mixture is then removed from the surgical or wound site. In the case of heavy bleeding caused by a ruptured artery or the like, it will be appreciated that the mixture removed may be comprised of primarily blood. The blood-fluid mixture is drawn up using a submersible suction tip 18. The submersitle suction tip 18 conveys the blood fluid mixture into suction tube 20. Suction tube 20 conveys the mixture to collection vessel 22. Collection vessel 22 may include a bubble detector (also known as blood-level detector) 24, such as a commercially available ultrasonic bubble detector. When bubbles are detected in tube 20, the bubble detector 21 acts on the blood pump described below to decrease its speed so that no further air bubbles are drawn into the suction tube 20. Also associated with this bubble detector is a blood pump speed controller, also shown at 21, for controlling the speed of input into the collection vessel 22. This controller also regulates the speed of fluid pump 14, and plasma pumps 40 and 46. As described below. The controls may also control addition of protamine or a similar substance to the reinfused blood.

The collection vessel 22 may also comprise a macrofilter to catch large particles which may flow into the collection vessel 22. Any type of conventional macrofilter is usable. It is presently preferred that such a macrofilter have a pore size in the range of from approximately 150 to approximately 40. Such filters are manufactured by numerous manufacturers including Pall Filters, Gellman and Micro Filtration Systems. The macrofilter will remove any tissue fragments, blood clots, or other types of emboli at this point in the process.

In association with collection vessel 22 there may also be a blood level detector and control mechanism 24. The blood level detector is designed to maintain the blood level at a predetermined level. If the blood level dropped below this predetermined level, a source of fluid begins to flow through fluid line 33 into the collection vessel and an air vent mechanism 25 opens such that air is removed from the collection vessel 22 and the fluid level returns to an acceptable level.

The blood fluid mixture leaves the collection vessel 22 through collection vessel outlet line 26. It will be appreciated that a blood pump 28 may be disposed on the collection vessel outlet line 26 in order to provide sufficient suction to move the blood-fluid mixture through the apparatus to this point. It is anticipated that one acceptable type of blood pump is a conventional roller pump. The roller pump provides sufficient suction without providing the high levels of vacuum which cause homolysis, blood damage, and other problems in the existing art.

The blood fluid mixture then flows into a filter vessel 30. Disposed within the interior of the filter vessel 30 is a membrane plasma separator. The membrane plasma separator may be any type of filter conventionally used in the art. It is presently preferred that the filter have a pore size in the range of from approximately $0.2\mu$ to approximately $0.5\mu$ with a minimum surface area of approximately $0.3 m^2$. Such filters are manufactured by various manufacturers including Cobe Labs, Travenol Labs, Fresenius A. G., and Asahi. The filter vessel 30, along with membrane plasma separator causes the plasma and excess fluid (fluid added at the wound site) to be separated from the blood cells. As mentioned above, the blood cells will still contain sufficient plasma to keep the blood cells suspended. It is presently preferred to maintain the transmembrane pressure across the filter at below approximately 100 mm Hg such that hemolysis is avoided.

The blood cells leave the filter vessel 30 through blood cell outlet line 32. The blood cells may be introduced immediately to the patient. Alternatively, the blood cells may be mixed with plasma prior to reinfusion. That plasma is preferably plasma obtained by the process of the present invention.

Plasma leaves the filter vessel 30 through plasma outlet line 34. The plasma outlet line 34 may flow through an optional hemoglobin detector 36. In the event that unacceptably high levels of hemoglobin are detected at this point, the plasma will be discarded through discard line 38. In the event that the plasma is found to be acceptable at this point, the plasma continues through plasma outlet line 34 which passes through an optional plasma line pump 40 into an ultrafiltration vessel 42.

Ultrafiltration vessel 42 contains an ultrafilter. The ultrafilter preferably has a pore size cut off of approximately 60,000 daltons such that the excess fluid which was added at the wound site and activated coagulation factors are separated from the remaining plasma. The filtrate will primarily comprise the Ringer's or saline solutions originally introduced to the surgical or wound site.

It will be appreciated that the transmembrane pressure may be as high as approximately 500 mm Hg (or as recommended by the filter manufacturer) because of the fact that blood cells have been removed from this mixture and, therefore, there is no potential hemolysis or other cell damage. Pressures can be monitored continuously and an alarm provided in the event pressures become excessive. It should also be noted that most of the anticoagulant (heparin) will leave the plasma at this point.

Plasma will leave the ultrafiltration vessel 42 and flow through an optional multiadsorbent bed 44. The multiadsorbent will adsorb toxins which remain within the plasma. Acceptable types of multiadsorbents for use in the present invention include: activated carbon (charcoal) granules; XAD amberlite resins; ion exchange resins; immunosorbents; heptogloblin-agarose adsorbent; and heparin adsorbents.

The plasma then continues through an additional plasma line pump 46 into a mixing vessel 48 which is shown at the 22 intersection of the plasma outlet line 34 and the blood cell outlet line 32. The recombined blood cells and plasma are then preferably reintroduced into the patient through a bubble detector.

It will be appreciated that the present invention accomplishes the objects set forth above. Importantly, air interfaces within the device and throughout the process are minimized. At the same time, there is no high vacuum produced and resulting hemolysis, protein denaturation, foaming, and other damage to the blood is avoided. Using the present invention, blood is processed and reintroduced to the patient immediately via tubing to the patient's vascular system at the surgical site. No delays of the type generally encountered in blood washing techniques are experienced using the present invention. In addition, conventional inexpensive, components can be used in the present invention. Thus, it is presently anticipated that the present invention will cost much less than conventional blood washing and autotransfusion systems.

Figure 2:
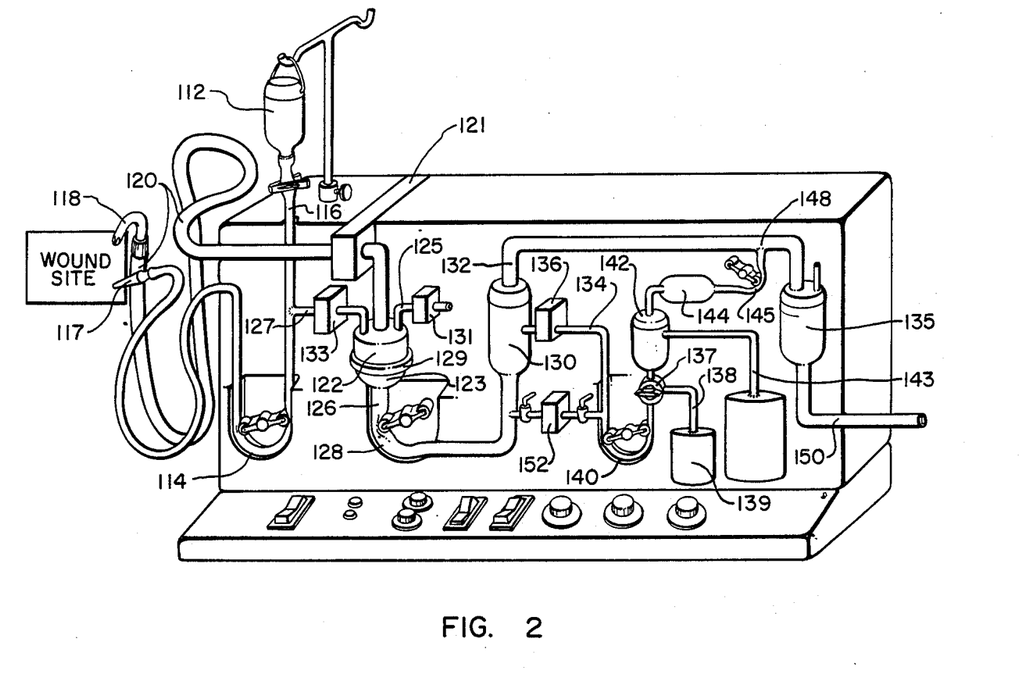
FIG. 2 is a perspective view of one embodiment of the apparatus of the present invention.

The apparatus of the invention can be more fully understood with reference to FIG. 2. FIG. 2 is a general perspective view of one embodiment of the apparatus of the present invention. The apparatus illustrated in FIG. 2 contains essentially the components described with reference to FIG. 1. For example, the apparatus described in FIG. 2 includes a source of fluid 112. The source of fluid 112 may comprise a simple conventional bottle containing heparinized saline, Ringer's solution, or other similar type of fluid generally used in surgical and medical applications. It will be appreciated that sufficient anticoagulant, such as heparin, will be added to the fluid to prevent coagulation of blood within the system.

The fluid contained in the fluid source 112 flows into fluid supply line 116. The fluid in fluid supply line 116 may be driven by a fluid pump 114. As illustrated in FIG. 2, fluid supply line 116 terminates at the surgical or wound site. In the illustrated embodiment a conventional nozzle 117 is attached to the end of fluid supply line 116. It will be appreciated that nozzle 117 provides the surgical personnel with control over the direction and speed of flow out of the fluid supply line 116. Thus, the intensity with which the stream hits a particular area can be controlled. Likewise, the direction of flow can be more easily controlled. Other types of nozzles may also be used, some of which are described below.

A resulting blood fluid mixture accumulates at the wound site. This mixture is then removed from the surgical or wound site, flowing into a submersible suction tip 118. Submersible suction tip 118 allows the accumulated fluid to be removed without removing a significant amount of air. Once the fluid-blood mixture enters suction tip 118 it is conveyed into suction line 120. Suction line 120 may flow through a bubble detector and controller 121 such that the quantity of air within the blood-fluid mixture can be immediately determined.

An ultrasonic bubble detector is presently preferred and is of the type that is commercially available. The bubble detector may be placed in contact with the blood pump such that any air bubble in the line would reduce the pump speed so that no more air will subsequently be drawn into the device. In addition, if excess bubbles are detected, the bubble detector 121 will provide the surgical team with immediate notice to adjust the method of collection of the fluid at the wound site.

Suction line 120, as well as the other tubing comprising the apparatus of the present invention, may include any type of conventional, biocompatible medical tubing. The specific diameter and chemical formula of the tubing may vary depending on the specific use and/or convenience. Such tubing may include polyvinyl chloride (PVC), polyurethane, silastic or polyethylene material.

The blood-fluid mixture is then conveyed by suction line 120 to collection vessel 122. It is presently preferred that the end of suction line 120 terminates by passing the flow of fluid through a macrofilter 123. The macrofilter will immediately remove any particulate debris from the blood fluid mixture. The macrofilter will preferably have a pore size of between approximately $40\mu$ and approximately $150\mu$ and can be obtained from the manufacturers such as Pall, Gellman and Micro Filtration Systems.

Also illustrated in connection with collection vessel 122 is a fluid level detector and adjustment mechanism. When the fluid level drops below a particular predetermined level, vent 125 will be opened through valve 131 and fluid will be introduced into the collection vessel through fluid line 127 by way of valve 133. Fluid level detector 129 may be any type of conventional fluid level detector such as that manufactured by Renal Systems, Inc.

It will be appreciated that fluid through fluid line 127 will flow into the collection vessel 122 until a sufficient level of fluid is contained within the vessel. At that point, the vent will be closed and the flow of fluid through line 127 will be terminated.

As illustrated in FIG. 2, the blood-fluid mixture leaves the collection vessel 122 through the collection vessel outlet line 126. Suction may be provided to the system to this point through blood pump 128. As mentioned above, blood pump 128 may also be a conventional roller pump. Roller pumps provide sufficient suction, without providing unwanted high vacuum, and also are able to operate without significant damage to the fluid within the subject line.

As illustrated in FIG. 2, the collection vessel outlet line terminates at filter vessel 130. Filter vessel 130 contains a membrane plasma separator. The separator comprises a filter apparatus for separating plasma from blood cells. The filter will preferably comprise a conventional filter having a pore size of between approximately $0.2\mu$ and $0.5\mu$. Plasma separation will preferably take place due to a pressure difference of less than approximately 100 mm Hg.

Once the blood cells and plasma are separated, the blood cells leave the filter vessel 130 through blood cell outlet line 132. Plasma leaves the filter vessel 130 through plasma outlet line 134. Plasma outlet line 134 then flows through an optional hemoglobin detector 136. If it is determined that the plasma contains an unacceptably large amount of hemoglobin, the plasma will be directed through three-way valve 137 into plasma discard line 138 into a waste vessel 139 or other similar type of disposal apparatus.

In the event that the plasma is found to be acceptable, the plasma will flow along plasma outlet line 134. Outlet line 134 then passes through plasma pump 140 which may also be a conventional roller pump. Plasma outlet line 134 then proceeds into an ultrafiltration vessel 142. Ultrafiltration vessel 142 contains an ultrafilter having a pore size cut off of 60,000 daltons such that the fluid, including most of the heparin and activated coagulation factors are removed from the mixture. An acceptable ultrafilter can be obtained from the manufacturers listed above.

The low molecular weight fluid leaves the vessel through disposal line 143. The lower molecular weight fluid essentially comprises the initial saline or Ringer's solution introduced at the wound site and the activated coagulation factors. This will leave essentially plasma alone.

It may be desirable to have plasma outlet line 134 continue to flow through a multiadsorbent chamber 144. The multiadsorbent chamber 144 will contain a multiadsorbent bed such as that described above. The multiadsorbent will remove from the plasma toxins which may have accumulated in the plasma during the entire process.

Plasma outlet line 134 then continues through an additional roller pump 145 into mixing area 148. At this point it is possible to mix the plasma with the washed blood cells. This mixture may then be reinfused into the patient.

As will be appreciated with reference to FIG. 2, the blood cell outlet line continues out of filter vessel 130 through a bubble detector 135. Bubble detector 135 may also include a vent mechanism to vent any bubbles which may accumulate at this point in the line. Blood cell outlet line 132 then continues into mixing area 148 where the blood cells are recombined with the plasma for reinjection through patient infusion line 150.

Also illustrated in FIG. 2 are various controls on the pumps involved. These generally include speed controls for each of the pumps. In addition, pressure control 152 may be added to the various lines in order to release excessive pressure within the subject lines or to detect that pressure prior to excess buildup.

In addition, flow rate controls are provided. The system may be set such that a lower limit of fluid flow is determined (such as about 15 cc/min.). In the event of a surge of bleeding the system may be provided with manual controls, such as a foot pedal or button, to allow the surgeon to greatly increase flow. Thus, flow can be adjusted as needed. Alternatively, automatic controls, of the type described below, may be employed.

Figure 3:
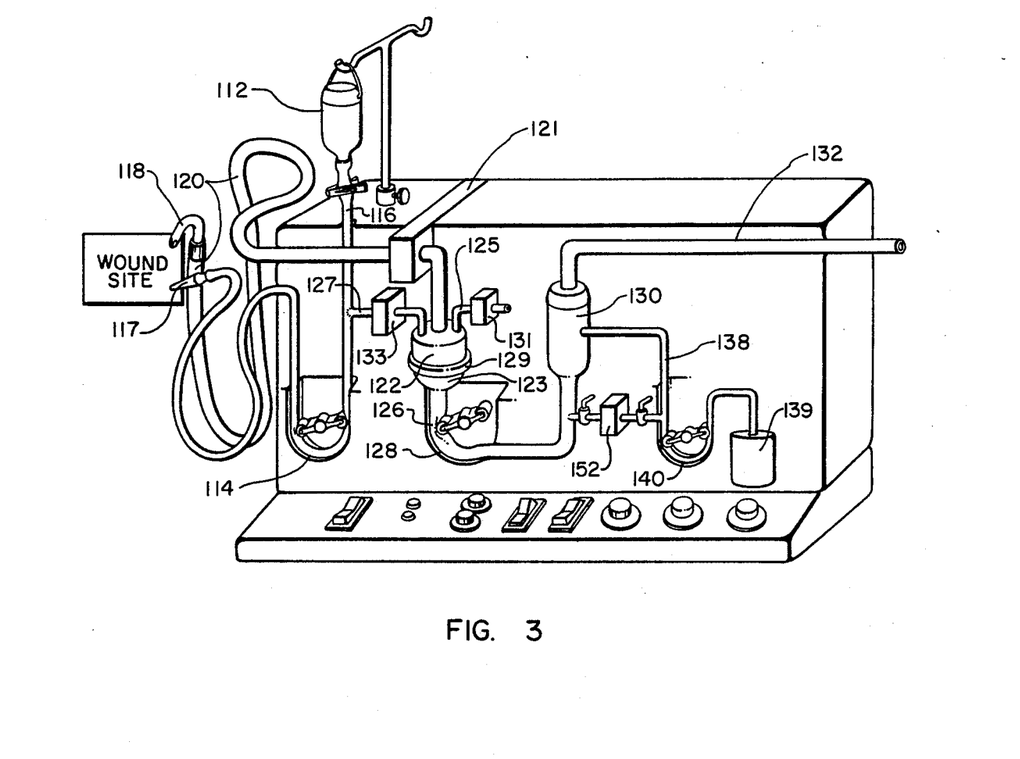
FIG. 3 is a perspective view of an abbreviated embodiment of the apparatus shown in FIG. 2.

FIG. 3 illustrates the same system as that illustrated in FIG. 2 except that the system is abbreviated. In the system shown in FIG. 3 the plasma and the fluids are both discarded. In this system, only the blood cells are washed and returned to the patient.

FIG. 3 illustrates further the flexibility of the system. If, upon examination, the surgeon determines the blood condition justifies, he may elect to return the shed whole blood direct to the patient without separating out any blood components. If, upon examination, the surgeon determines there is cell damage sufficient to justify separation from other components, he may elect to do so and discard all but the viable cells. Further, if, upon examination, the surgeon determines retaining of plasma is desired, he may do so and recombine with the cells for immediate return, discarding other fluids.

The method of operation of the present invention is readily appreciated with reference to FIGS. 1 and 2. A controlled stream of clear fluid such as heparinized saline or Ringer's solution will be introduced to the wound site from a fluid supply 116 through nozzle 117. The mixture of fluid and blood will then be removed through suction tip 118 into suction line 120. In the case of very heavy bleeding it will be appreciated that the mixture is composed primarily of blood. Suction tip 118 will be submerged in order to avoid any blood air mixing and interaction. Thus, the only blood air interface will be that found at the wound site.

The blood-fluid mixture will then be drawn into suction line 120 where bubbles may be detected using a bubble detector 121. The blood-fluid mixture will then be introduced into a collection vessel where any excess air will be vented through vent 125 through the use of an automatic fluid level detector 129.

Once the mixture has been collected, and any air settled out and removed, the mixture will leave the collection vessel through collection vessel outlet line 126 and flow into filter vessel 130. Within filter vessel 130, the blood cells and the remaining fluid are separated. The blood cells may be reintroduced into the patient alone. Alternatively, the blood cells may be mixed with plasma prior to reintroduction to the patient.

Plasma separated from the mixture can also be recovered. The plasma will flow through a hemoglobin detector to determine whether there is a significant amount of hemoglobin in the plasma. If there is not, the plasma will flow into an ultrafiltration vessel 142 wherein the plasma and remaining fluids will be separated. The unwanted fluid can be discarded and the plasma can then be collected, mixed with the processed blood cells, or introduced to the patient alone.

In certain cases it will be desirable to directly reinfuse the blood obtained at the wound site. In cases such as rapid bleeding from a ruptured artery, it may be desirable to bypass some of the steps described above and flow the collected blood directly back to the patient. In such cases the filtering and separation mechanism can be bypassed or minimized in order to provide immediate use of the blood collection.

Figure 4:
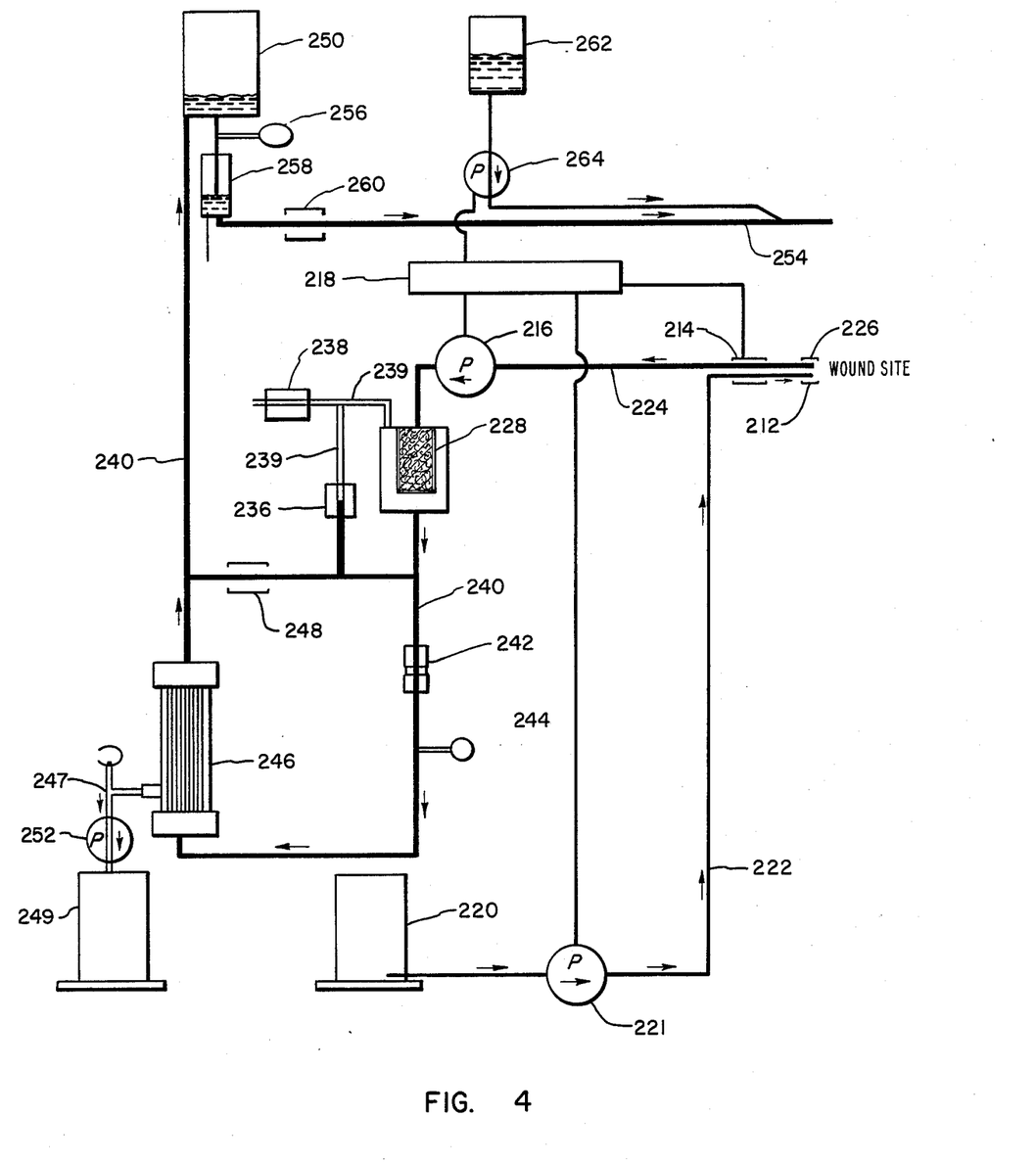
FIG. 4 is a schematic diagram illustrating another embodiment of the apparatus and methods of the present invention.

An additional modified embodiment of the present invention is illustrated in FIG. 4. The embodiment of the invention illustrated in FIG. 4 allows one to automate many of the functions described above. In addition, the embodiment of the device in FIG. 4 minimizes blood damage, while returning blood to a patient on a real time basis.

The embodiment illustrated in FIG. 4 provides automatically controlled suction of shed blood from the wound site in proportion to the bleeding rate. In addition, the washing fluid and anticoagulant flow to the wound site is in proportion to the bleeding rate. This is accomplished by providing a bubble detector 214, such as an ultrasonic or optical infrared transducer, attached to the suction tip 212. As soon as a bubble is detected within the suction tip at the bubble detector 214, the speed of the suction pump 216 is reduced. The pump speed continues to be reduced until no air is detected by the bubble detector 214.

When the pump slows to the point where no air is detected by bubble detector 214, the suction pump 216 speeds up slightly until a small bubble appears at the suction tip, at which time the pump again slows. The bubble detector and the various pumps in the system may be placed in communication by means of a microprocessor 218 programmed to follow this logic step. Essentially the bubble detector determines whether or not there is a bubble in the suction tip. If the answer is yes, the pump speed is decreased. If the answer is no, the pump speed is increased. This microprocessor program and control mechanism may also be placed in communication with the remainder of the pumps in the device so that the entire apparatus 210 operates at a speed proportional to the bleeding rate monitored by the bubble detector 214.

This embodiment of the present invention also provides for processing diluted blood on a real time basis without any manual intervention. That is, the processed blood flowing through the apparatus flows at a rate proportional to blood flowing into the apparatus. If bleeding increases at the wound site, blood is processed and returned to the patient at a higher rate. If bleeding slows, the rate of processing also slows. Thus, the patient is provided with blood for infusion at precisely the required rate.

The objectives set forth above are all accomplished by the apparatus 210. As mentioned above, a suction tip 212 of the type described herein is provided. The suction tip 212 is placed in communication with the wound site. Fluid then flows to the wound site from a source of fluid 220 under the force of fluid pump 221. The fluid may flow through a fluid supply line 222.

In the illustrated embodiment, the fluid supply line 222 terminates in a suction tip 212 which also contains an attachment for suction line 224. As will be described in further detail below, in one preferred embodiment, the fluid supply line 222 and the suction line 224 are coterminus and are encased in a shroud 226. Thus, a constantly flowing supply of fluid flows from the end of fluid supply line 222 and is immediately drawn into suction line 224 by the constant vacuum produced by suction pump 216. Thus, mixing between air and the blood drawn into the line is avoided. The blood flows immediately into a supply of fluid at the end of the suction tip 212 rather than into a mass of flowing air as is conventional in the art.

As mentioned above, the blood and fluid mixture is drawn into suction line 224 by means of suction. One preferred means of suction, is a suction pump 216 which may, for example, be a conventional roller pump. It will be appreciated, however, that the suction provided by suction pump 216 is much less than that used in conventional devices. Accordingly, blood damage due to high levels of vacuum is avoided.

Suction line 224 terminates in a filter container 228. The filters within container 228 provide primary filtration of blood to remove macroparticles, generally above 40 microns in size. The filter canister is also provided with means for the automatic venting of any small volumes of air which may travel with the blood to this point in the circuit.

Figure 5:
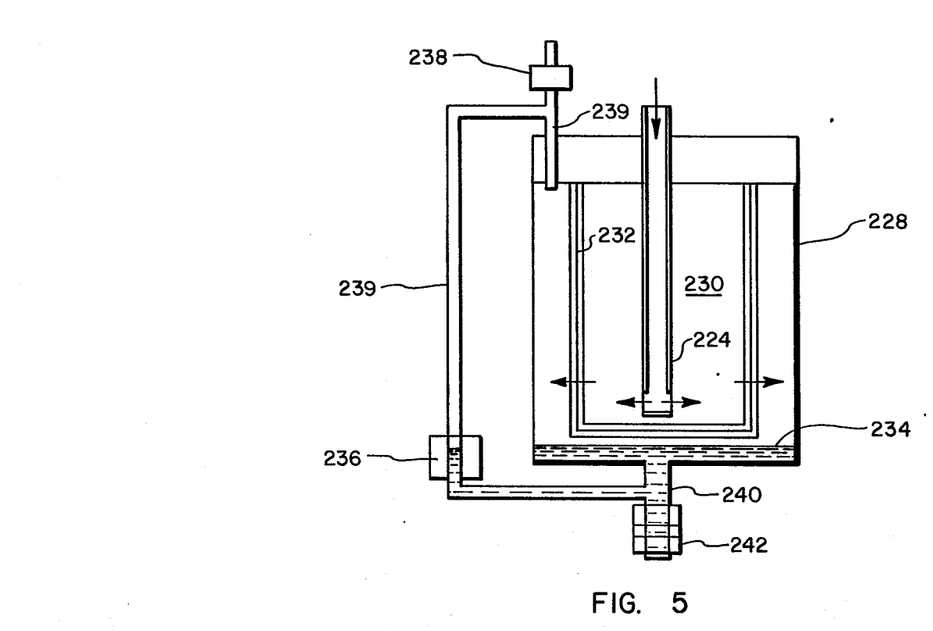
FIG. 5 is a schematic diagram illustrating the macrofilter and air vent portion of the system shown in FIG. 4.

The operation of filter canister 228 can be more fully understood with reference to FIG. 5. In FIG. 5, the filter canister 228 and its various components are illustrated. Suction line 224 terminates near the bottom of canister 228. The blood and fluid mixture flows through suction line an 224 filling an interior area 230 within canister 228. It will be appreciated that any air that is contained within the blood at this point will be allowed to rise to the top of the interior area 230.

Blood and fluid are then filtered through three layers of filter 232, with each layer of filter having a decreasing pore size. For example, in one embodiment, a polyester fiber having 20 pores per inch forms the initial filter. This layer may be coated with an antifroth compound (such as Dow Corning antifroth silicone compound). Blood then flows through another polyester fabric filter having a 160 micron pore size, and finally travels through a fine polyester fabric with a 40 micron pore size. It may also be advisable to coat the filter layers with antifoam agents which will further help to remove any air from the blood. It should also be noted that the blood flows from a higher pressure area to a lower pressure region, thus further helping with the degasifying process.

As illustrated in FIG. 5, a certain blood level 234 is maintained within the device. As air accumulates on top of the fluid layer, the blood level 234 will drop. Thus, the device is also provided with a blood level detector 236. Blood level detector 236 may be an ultrasonic blood level detector or any other conventional fluid level detector. When the blood level reaches a particular chosen level, an air vent 238 is opened. As can be seen from FIG. 5, air vent 238 is placed in communication with the interior of the filter canister 228 and also with the blood level detector 236 through air lines 239.

Thus, air is simultaneously vented from both sources and the fluid levels remain equal.

As mentioned above, when air vent 238 is opened, air is allowed to escape and fluid is allowed to fill the interior of canister 238 above the critical blood level 234. At this point, the valve closes and the operation of the device continues.

Once the blood and fluid mixture has been filtered for macroparticles, the mixture leaves the filter canister 228 through outlet line 240. During normal operation, the blood and fluid mix may flow through a hematocrit indicator 242 and a pressure gauge 244. Hematocrit indicator 242 can be any device of the type known in the art for measuring hematocrit in a fluid.

The purposes of hematocrit indicator 242 and pressure gauge 244 is to monitor the fluid flowing in line 240. Hematocrit indicator 242 determines exactly how much irrigation fluid has been added to the wound site so that it can be removed from the recovered blood. In the event that a massive hemorrhage takes place, the fluid flowing in line 240 will comprise primarily blood. The flow rate of blood through the ultrafilter 246, as illustrated in FIG. 4, will increase causing an increase in pressure at the inlet of the ultrafilter 246. When the pressure in the line 240 rises above a predetermined maximum limit (for example 400 mm Hg), a bypass valve 248 will open. This allows the fluid (primarily filtered blood) to return directly to the venous blood reservoir 250. Thus, the blood can be returned directly to the patient without further processing through the ultrafilter in that further removal of fluids from the blood is unnecessary because the fluid flowing through the device comprises primarily blood.

In the normal operation of the device, however, the blood will continue through line 240 into ultrafilter 246. Ultrafilter 246 provides secondary filtration of the diluted blood to remove irrigation and washing fluids, plasma-free hemoglobin and activated coagulation factors. The technique of ultrafiltration or plasma separation is well known in the art. The filtration rate is generally determined by the filter membrane pore size distribution and fluid shear rate at the membrane. The shear rate can be varied by recirculating blood through the ultrafilter using an additional pump if desired for specialized applications. The transmembrane pressure within ultrafilter 246 may be varied by a suction pump 252 placed on the filtrate side of the ultrafilter 246.

Fluids filtered out of the stream by ultrafilter 246 leave the system through outlet line 247. Fluids then continue into disposal container 249. Flow into disposal container 249 is also regulated by suction pump 252.

It is generally known that during surgery, the amount of fluids placed in the surgical site is not closely monitored. For example, washing or irrigation fluids are used as extensively as necessary to maintain a clear surgical area, without close monitoring of the volume of washing fluids. Accordingly, an unknown variable in the filtration process is the amount of added fluid at the surgical site. The hematocrit indicator continuously monitors the blood at the inlet to the filter. Hematocrit is a direct measure of the percentage of washing fluid in the blood in that increase washing fluid directly decreases the hematocrit. The speed of the filtrate pump is varied inversely proportionally to the hematocrit measured by the hematocrit indicator impedance meter electrodes. Using this method, secondary filtration is controlled and operates automatically. Secondary filtration is not dependent on the bleeding rate, the irrigation fluid rate, or any of the other variables in the system.

Once the blood is fully filtered it leaves ultrafilter 246 and continues through line 240 into venous blood reservoir 250, already mentioned above. Venous blood reservoir 250 is primarily a collection vessel for the filtered blood. As illustrated in FIG. 4, blood preferably flows into venous blood reservoir 250 through its base in order to avoid any unnecessary blood-air mixing.

The blood in venous blood reservoir 250 is ready to be reinjected into the patient. Blood flows out of venous reservoir 250 through blood return line 254. Blood return line 254 may have a pressure indicator 256 and bubble detector 258. In the event air bubbles are detected at this point in the process, a valve 260 will close to stop the flow through the system.

It will be appreciated that heparin or other similar anticoagulant will have been added to the collected blood in order to prevent coagulation inside of the apparatus 210. However, an excess of anticoagulant injected back to the patient is not desired. This may increase the bleeding rate of the patient to dangerous levels. Accordingly, a reservoir filled with an appropriate chemical substance, such as protamine, to counteract the effects of the anticoagulant is shown at 262. Flow rate out of the reservoir 262 is controlled by pump 264. Pump 264, in turn, is controlled by the microprocessor unit 218 and its rate of operation is tied directly to the flow rate of the overall system, particularly the injection rate of the washing fluid containing anticoagulant from fluid source 226. Therefore, precise amounts of the needed substance used to counteract the anticoagulant is provided automatically. Once this component is added, the blood may be returned directly to the patient through blood return line 254.

The device illustrated in FIG. 4 provides numerous advantages. Each of the pumps incorporated into the system is regulated through microprocessor 218. The pumps, in turn, respond to changes in the amount and character of the blood-fluid mixture flowing in the system. For example, feedback from bubble detector 214 controls the rate at which washing fluid is introduced to the wound site, the rate at which processed blood returns to the patient.

In addition, air is automatically vented from the system. When excessive volumes of air accumulate in filter container 228, air vent 238 automatically opens in response to a signal from blood level detector 236. Likewise, when a very high concentration of blood is detected by hematocrit indicator 242, bypass valve 248 opens. This allows fluid that comprises primarily blood to return rapidly to a hemorrhaging patient. No manual adjustments are needed from the busy medical staff.

Figure 6:
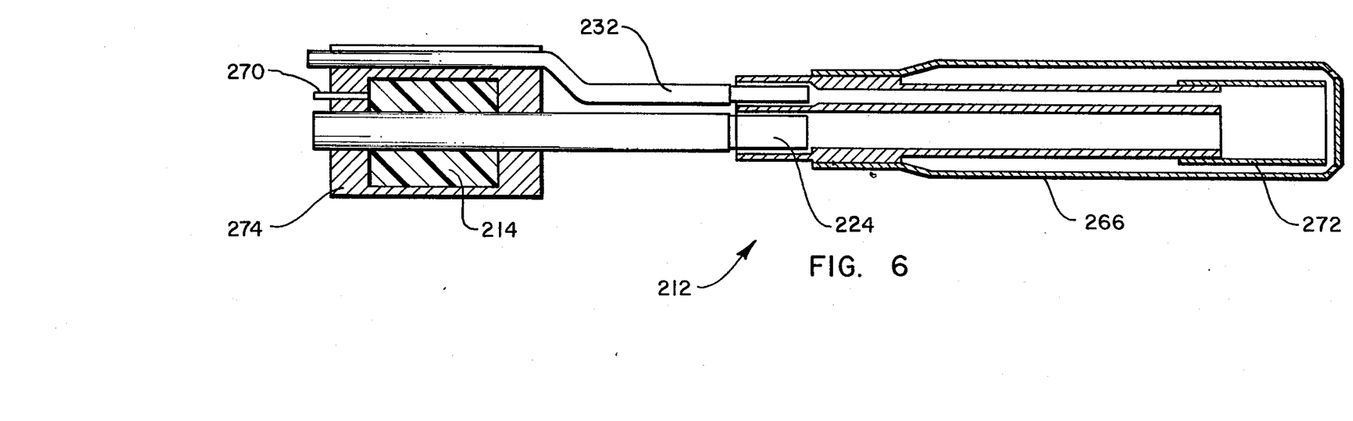
FIG. 6 is a longitudinal cross-sectional view of one embodiment of a suction tip to be used in the apparatus of the present invention.

A final aspect of the present invention is a unique suction tip for drawing blood into the apparatus without the necessity of a blood-air interface. Reference is now made to FIG. 6. FIG. 6 is a longitudinal cross-sectional view of suction tip 212. As can be appreciated from FIG. 6, suction tip 212 acts as the terminus of both fluid supply line 222 and suction line 224. The ends of fluid supply line 222 and suction line 224 are held within the interior of shroud 272. Also illustrated in FIG. 6 is a porous shield 266. Porous shield 266 is preferably removable from suction tip 212. Moreover, porous shield 266 prevents tissue and other solid material from being drawn into the suction tip during operation. Porous shield 266 may be of any one of numerous known configurations of shields of this type.

Also illustrated in FIG. 6 is a bubble detector 268 embedded within the handle 274 of the suction tip 212. The bubble detector 214 may, for example, be a conventional ultrasonic bubble detector. As mentioned above the bubble detector 214 provides immediate feedback to the microprocessor 218 to control the rate of flow of fluid through the entire device. The ultrasonic bubble detector transducer is placed in electrical communication with the appropriate mechanism through connecting cord 270.

The method of operation of suction tip 212 can be easily understood with reference to FIG. 6. Fluid flows to the end of suction tip 212 through fluid supply line 222. Fluid exits the end of the tip, but is immediately drawn back into suction line 224. The result is a dynamic droplet at the end of the suction tip 212 which represents a constant flow of fluid from line 222 into line 224. This dynamic droplet is maintained in place by shroud 272 which encloses the ends of both lines.

As a result of the dynamic droplet, blood entering the overall device flows immediately into a liquid environment. No mixing between the blood and air is necessary as the blood flows into the device. Thus, a major source of damage to recovered blood is eliminated.

As the blood-fluid mixture flows up through suction line 224, any air bubbles in the mixture are detected by bubble detector 214. Accordingly, immediate feedback is provided to microprocessor 218 to make the needed adjustment in the level of suction.

Accordingly, it will be appreciated that the suction tip 212 of the present invention provides a significant advancement in the art. The suction tip allows blood to be drawn into the device without the necessity of an immediate blood-air mixture. In addition, the ultrasonic bubble detector allows any air to be immediately detected and feedback given to a microprocessor unit. This feedback is then used to increase or decrease the rate of suction. Accordingly, excessive air intake is immediately compensated for.

SUMMARY

It will be appreciated that the present invention accomplishes all of the objects set forth above. The present invention provides a mechanism whereby blood lost during an operation or as a result of an injury can be recovered and reintroduced into the patient. All of this processing can take place essentially simultaneously with the patient's immediate need. There is no significant delay in the processing of the blood, as is normally encountered in autotransfusion and blood washing techniques.

At the same time, the present invention avoids the air mixing which generally occurs when using high vacuum systems. The submersible suction tip allows blood to be removed from the surgical site without significant air mixed within the blood-fluid mixture. In addition, blood-air interfaces are avoided throughout the system. The system provides for venting of any accumulated air at critical points In addition, bubble detectors may be located on the system at any desired location.

Thus, it can be seen that the present invention provides a vast improvement over existing devices. Blood may be salvaged and reintroduced into the patient without the need for providing great amounts of homologous blood. Thus, the problems associated with the use of homologous blood are avoided. At the same time, the present invention is extremely inexpensive and uses simple conventional components. As a result, the economics of using the autotransfusion system of the present invention are extremely favorable.

It will be appreciated that the apparatus and methods of the present invention are capable of being incorporated in the form of a variety of embodiments, only a few of which have been illustrated and described above. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. A system for collecting shed blood from a patient and for subsequently reintroducing that blood to the patient, comprising:
   means for introducing a controlled stream of fluid to a wound site containing blood;
   means for removing the resulting mixture of blood and fluid from the would site such that substantially only the mixture is removed and such that significant amounts of air are not removed with said mixture, said removal means comprising a suction tube in communication with means for causing suction within said suction tube, and an air detector for detecting air in the mixture of blood and fluid removed, said air detector being in communication with said suction means such that suction can be varied based upon the presence or absence of air in the mixture;
   means for removing particulate impurities from the mixture;
   means for removing excess fluid from the mixture such that substantially only blood remains; and
   means for reinfusing the blood to the patient.

2. A system for collecting shed blood from a patient as defined in claim 1 wherein said means for removing the blood fluid mixture comprises a submersible suction tip.

3. A system for collecting shed blood from a patient as defined in claim 1 wherein said means for removing the blood fluid mixture comprises a single roller pump in communication with said suction tube.

4. A system for collecting shed blood from a patient as defined in claim 2 wherein said means for introducing fluid comprises means for flowing fluid through said submersible suction tip.

5. A system for collecting shed blood from a patient, as defined in claim 4 wherein said suction tip comprises the terminal portion of a fluid supply line, which is configured such that it can carry fluid to the wound site, and the terminal portion of a suction line, which is configured such that it can carry the blood fluid mixture away from the wound site when suction is applied to said suction line.

6. A system for collecting shed blood from a patient as defined in claim 5 wherein said suction tip further comprises a shroud encircling the terminal portions of said fluid supply line and said suction line.

7. A system for collecting shed blood from a patient as defined in claim 1 wherein said means for introducing fluid comprises a source of fluid, a fluid supply line in communication with said source of fluid at one end and with the wound site at the other end, and means for causing fluid to flow in said fluid supply line.

8. A system for collecting shed blood from a patient as defined in claim 7 wherein said means for causing fluid to flow in said fluid supply line comprises a roller pump.

9. A system for collecting shed blood from a patient as defined in claim 1 wherein said means for removing particulate debris comprises at least one filter through which said blood fluid mixture is caused to flow.

10. A system for collecting shed blood from a patient as defined in claim 1 wherein said means for removing excess fluid comprises at least one ultrafilter through which said blood fluid filter is caused to flow.

11. A system for collecting shed blood from a patient as defined in claim 1 wherein said means for reinfusing blood comprises a venous blood reservoir for collecting blood after said blood has passed through said means for removing particulate debris and said means for removing excess fluid.

12. A system for collecting shed blood from a patient as defined in claim 11 wherein said means for reinfusing blood further comprises a blood return line in communication with said venous blood reservoir at one end and with the patient at the other end and means for causing blood to flow through said venous return line.

13. A system for collecting shed blood from a patient as defined in claim 1 wherein said fluid introduced comprises an effective quantity of anticoagulant.

14. A system for collecting shed blood from a patient as defined in claim 12 further comprising means for introducing an effective amount of protamine into said venous return line.

15. An autotransfusion circuit comprising:
means for introducing a controlled stream of fluid to a wound site containing blood, said means comprising a fluid source and a fluid supply line configured such that fluid can be transported from the fluid source to the wound site;
means comprising a suction line and a source of suction in communication with said suction line, for removing the resulting mixture of blood and fluid from the wound site, said means further comprising means for detecting air in the suction line and means for reducing suction in response to detected air in the suction line such that substantially only the mixture is removed and such that significant amounts of air are note removed with said mixture;
means for removing particulate impurities from the mixture;
means for removing excess fluid from the mixture such that substantially only blood remains;
means for reinfusing the blood to the patient; and
means for controlling the flow of blood and fluid into, through and out of the autotransfusion circuit, said means being configured such that the volume of fluid flow to the wound site is varied in response to the bleeding rate at the wound site.

16. An autotransfusion circuit as defined in claim 15 further comprising means for determining the amount of fluid introduced to the wound site.

17. An autotransfusion circuit as defined in claim 15 wherein said means for removing the mixture comprises a single roller pump in communication with a suction tube.

18. An autotransfusion circuit as defined in claim 15 further comprising means for continuously monitoring the hematocrit of the mixture recovered.

19. An autotransfusion circuit as defined in claim 18 further comprising means, in communication with said for monitoring hematocrit, for bypassing said means for removing excess fluid when a predetermined high bleeding rate is encountered.

20. An autotransfusion circuit as defined in claim 15 wherein said means for controlling flow comprises a microprocessor in communication with said means for introducing fluid and said means for removing said mixture.

21. An autotransfusion circuit as defined in claim 15 further comprising means for venting excessive air accumulated within said autotransfusion circuit.

22. An autotransfusion circuit as defined in claim 15 wherein said means for controlling flow further comprises means for introducing an anticoagulant to said wound site in proportion to the bleeding rate.

23. An autotransfusion circuit as defined in claim 15 wherein said means for controlling flow comprises means for reinfusing blood to the patient at a rate proportional to the bleeding rate of the wound site.

24. A continuous flow autologous blood circuit for preserving blood shed by a patient comprising:
means for introducing a controlled stream of fluid to a wound site containing blood;
means for removing the resulting mixture of blood and fluid from the wound site, said means comprising a suction tube in communication with means for causing suction within the suction tube, and air detection means for detecting air in the mixture of blood and fluid, said air detection means being in communication with said suction means such that the level of suction can be varied based upon the presence or absence of air in the mixture, said removal means being configured to operate such that substantially only the mixture is removed and that significant amounts of air are not removed with said mixture;
plasma separation means for separating the blood cells from the remainder of the mixture, leaving substantially only plasma and fluid in the mixture;
means for removing fluid from the mixture of plasma and fluid such that substantially only plasma remains; and
means for reintroducing said blood cells to the patient.

25. A continuous flow autologous blood circuit as defined in claim 24 further comprising means for combining the plasma and blood cells prior to reintroducing said blood cells to the patient.

26. A continuous flow autologous blood circuit as defined in claim 24 further comprising means for selectively reintroducing the blood fluid mixture directly to said patient.

27. A continuous flow autologous blood circuit as defined in claim 24 wherein said means for introducing a controlled stream of fluid to the wound site comprises a supply of fluid, a fluid supply line in communication with the supply of fluid and pump means in communication with the fluid supply line such that fluid is pumped from the supply of fluid through the fluid supply line.

28. A continuous flow autologous blood circuit as defined in claim 24 wherein said means for removing the mixture of blood and fluid from the wound site comprises a submersible suction tip, said suction tip being in communication with a source of suction.

29. A continuous flow autologous blood circuit as defined in claim 28 wherein said source of suction comprises a suction tube in communication with a blood pump.

30. A continuous flow autologous blood circuit as defined in claim 29 further comprising a collection vessel in communication with said suction tube.

31. A continuous flow autologous blood circuit as defined in claim 30 wherein said collection vessel comprises means for detecting the level of fluid within the collection vessel.

32. A continuous flow autologous blood circuit as defined in claim 31 wherein said collection vessel further comprises means for adjusting the level of fluid within the collection vessel.

33. A continuous flow autologous blood circuit as defined in claim 32 wherein said means for adjusting the level of fluid within the collection vessel comprises at least one vent and a source of fluid in communication with the collection vessel such that fluid can be selectively added and air can be selectively vented from the collection vessel.

34. A continuous flow autologous blood circuit as defined in claim 30 further comprising a macrofilter disposed within the apparatus such that blood and fluid collected is filtered prior to leaving the collection vessel.

35. A continuous flow autologous blood circuit as defined in claim 30 further comprising a collection vessel outlet line whereby fluid may flow from the collection vessel into said outlet line.

36. A continuous flow autologous blood circuit as defined in claim 30 further comprising a filter vessel in fluid communication with the outlet line.

37. A continuous flow autologous blood circuit as defined in claim 36 further comprising a blood pump in communication with the outlet line such that fluid in the outlet line is caused to flow from the collection vessel to the filter vessel.

38. A continuous flow autologous blood circuit as defined in claim 36 wherein said plasma separation means comprises a plasma membrane separator disposed within said filter vessel whereby blood cells are separated from fluid and plasma.

39. A continuous flow autologous blood circuit as defined in claim 38 further comprising a blood cell outlet line for carrying blood cells out of said filter vessel.

40. A continuous flow autologous blood circuit as defined in claim 39 further comprising a bubble detector located on said blood cell outlet line.

41. A continuous flow autologous blood circuit as defined in claim 39 further comprising a plasma outlet line for carrying plasma and fluids from said filter vessel.

42. A continuous flow autologous blood circuit as defined in claim 41 further comprising a hemoglobin detector on said plasma outlet line.

43. A continuous flow autologous blood circuit as defined in claim 41 wherein said means for removing fluid from the mixture of plasma and fluid comprises an ultrafilter in communication with the plasma outlet line for separating plasma from other fluids.

44. A continuous flow autologous blood circuit as defined in claim 43 further comprising a mixing chamber for mixing plasma obtained from the plasma outlet line with blood cells in the blood cell outlet line.

45. A continuous flow autologous blood circuit as defined in claim 44 wherein said means for reintroducing said blood cells to the patient comprises an autologous blood line for conveying the contents of the mixing chamber to the patient.

46. A continuous flow autologous blood circuit as defined in claim 43 further comprising a multiadsorbent to remove toxins from the plasma.

47. A method for recovering and reinfusing blood lost by a patient at a wound site, comprising the steps of:
 (a) introducing a controlled stream of fluid to the wound site containing blood such that a mixture of blood and fluid forms;
 (b) removing the resulting mixture using a submersible suction tip such that substantially only the mixture is removed and significant amounts of air are not contained within the mixture;
 (c) monitoring the recovered mixture for the presence of air in the mixture;
 (d) filtering the mixture such that substantially all particulate debris is removed from said mixture;
 (e) removing the excess fluid and activated coagulation factors from the mixture; and
 (f) reinjecting the blood into the patient.

48. A method for recovering and reinfusing blood as defined in claim 47 wherein the step of introducing a controlled stream of fluid to a wound site further comprises providing a source of fluid in communication with a pump for transporting the fluid to the wound site.

49. A method for recovering and reinfusing blood as defined in claim 47 wherein the step of removing the blood-defined fluid mixture further comprises attaching the submersible suction tip to a suction tube and placing the suction tube in communication with a source of suction.

50. A method for recovering and reinfusing blood as defined in claim 47 further comprising the step of controlling the rate of introduction of fluid to the wound site in response to the bleeding rate.

51. A method for recovering and reinfusing blood as defined in claim 47 further comprising the step of controlling the rate of removal of the mixture in response to the bleeding rate.

52. A method for recovering and reinfusing blood as defined in claim 47 further comprising the step of controlling the rate of reinjection in response to the bleeding rate.

53. A method for recovering and reinfusing blood as defined in claim 47 further comprising the step prior to step (d) of separating the blood cells from the fluid and plasma contained in the mixture.

54. A method for recovering and reinfusing blood as defined in claim 53 further comprising the step prior to step (f) of recombining the blood cells.

55. A method for recovering and reinfusing blood as defined in claim 54 wherein the step of separating the blood cells from the fluid and plasma comprises introducing the mixture to a plasma membrane filter capable of removing the blood cells from the plasma and fluid.

56. A method for recovering and reinfusing blood as defined in claim 54 wherein the step of removing the fluid from the plasma comprises introducing the plasma and fluid to an ultrafilter.

57. A method for recovering and reinfusing blood as defined in claim 47 further comprising the step of continuously monitoring the hematocrit of the recovered mixture.

58. A method for recovering and reinfusing blood as defined in claim 47 wherein the stream of fluid contains an anticoagulant.

59. A method for recovering and reinfusing blood as defined in claim 58 further comprising means for neutralizing the anticoagulant prior to reintroduction of the blood to the patient.

* * * * *